United States Patent [19]

Cholhan

[11] Patent Number: 5,336,228
[45] Date of Patent: Aug. 9, 1994

[54] CERVICAL MANIPULATOR FORCEPS

[76] Inventor: Hilary J. Cholhan, 141 San Gabriel Dr., Rochester, N.Y. 14610

[21] Appl. No.: 820,269

[22] Filed: Jan. 14, 1992

[51] Int. Cl.$^5$ .............................................. A61B 17/28
[52] U.S. Cl. .................................... 606/119; 606/207; 606/208; 81/304
[58] Field of Search ............................... 606/205–208, 606/170, 171, 174, 119; 81/304, 307

[56] References Cited

U.S. PATENT DOCUMENTS 5,059,198 10/1991 Gimpelson ...................... 606/207 X

FOREIGN PATENT DOCUMENTS 836545 4/1952 Fed. Rep. of Germany ...... 606/208

*Primary Examiner*—Michael H. Thaler
*Attorney, Agent, or Firm*—I. M. Bak-Boychuk

[57] ABSTRACT

A tenaculum useful in obtaining transvaginal manipulative retention of a cervix includes a first forcep piece extending into a forked set of tines offset vertically and then twisted to form an upper set of grasping edges aligned above the axis of the forcep piece for visual access to the cervix. A second forcep piece pivots within the crook between the first tines, flexing the tines inwardly in to course of the pivot, the second piece including a second tine pair at its end which through surface engagement at the pivot are also flexed inwardly. In this manner visual access to the cervix is provided in a structure which reduces in the grasping dimension with closure.

1 Claim, 2 Drawing Sheets

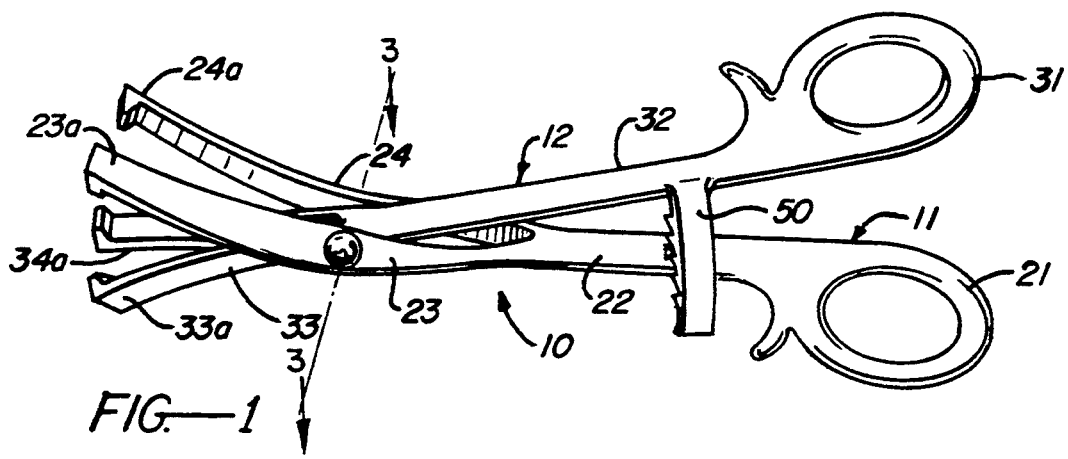
FIG.—1
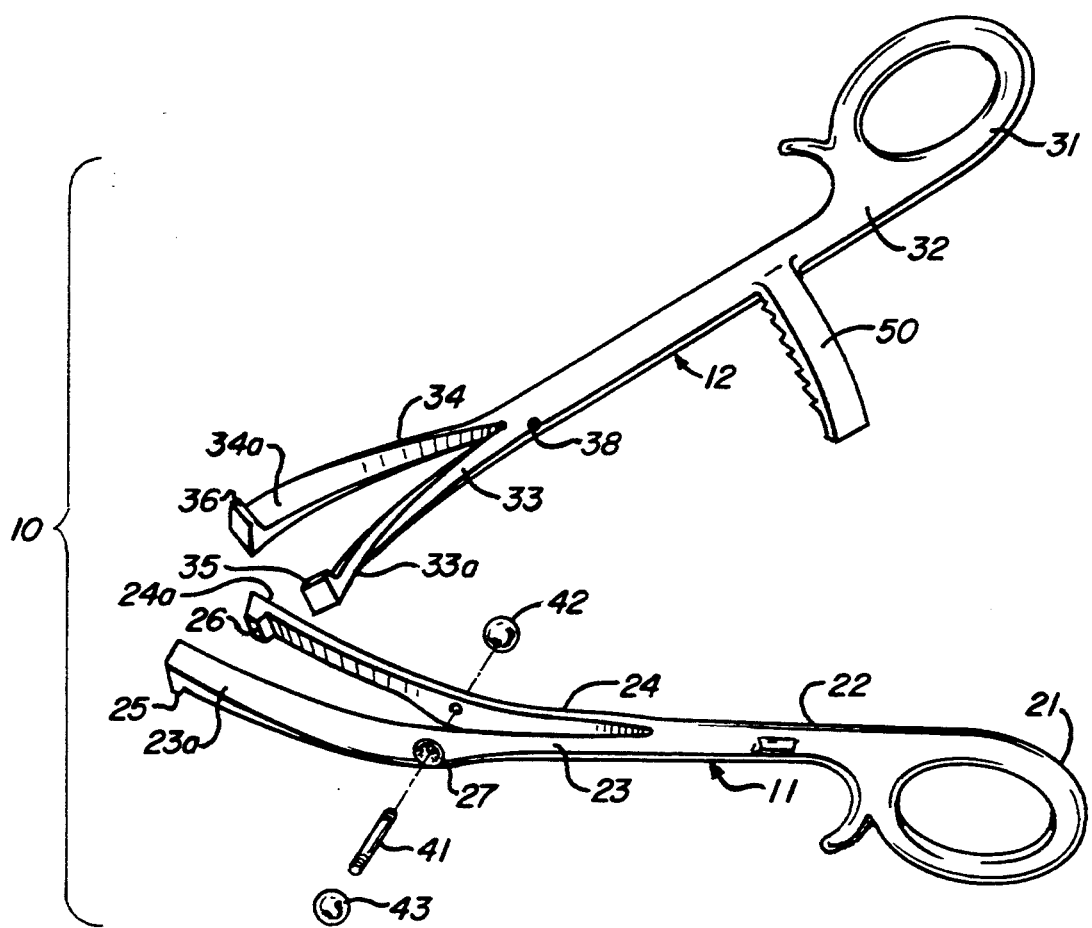
FIG.—2

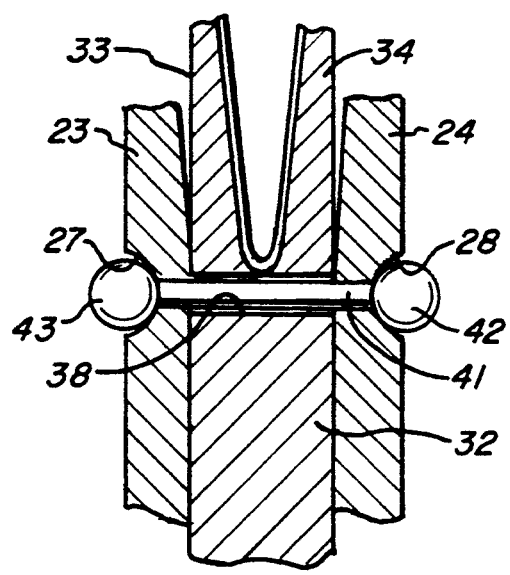
FIG.—3
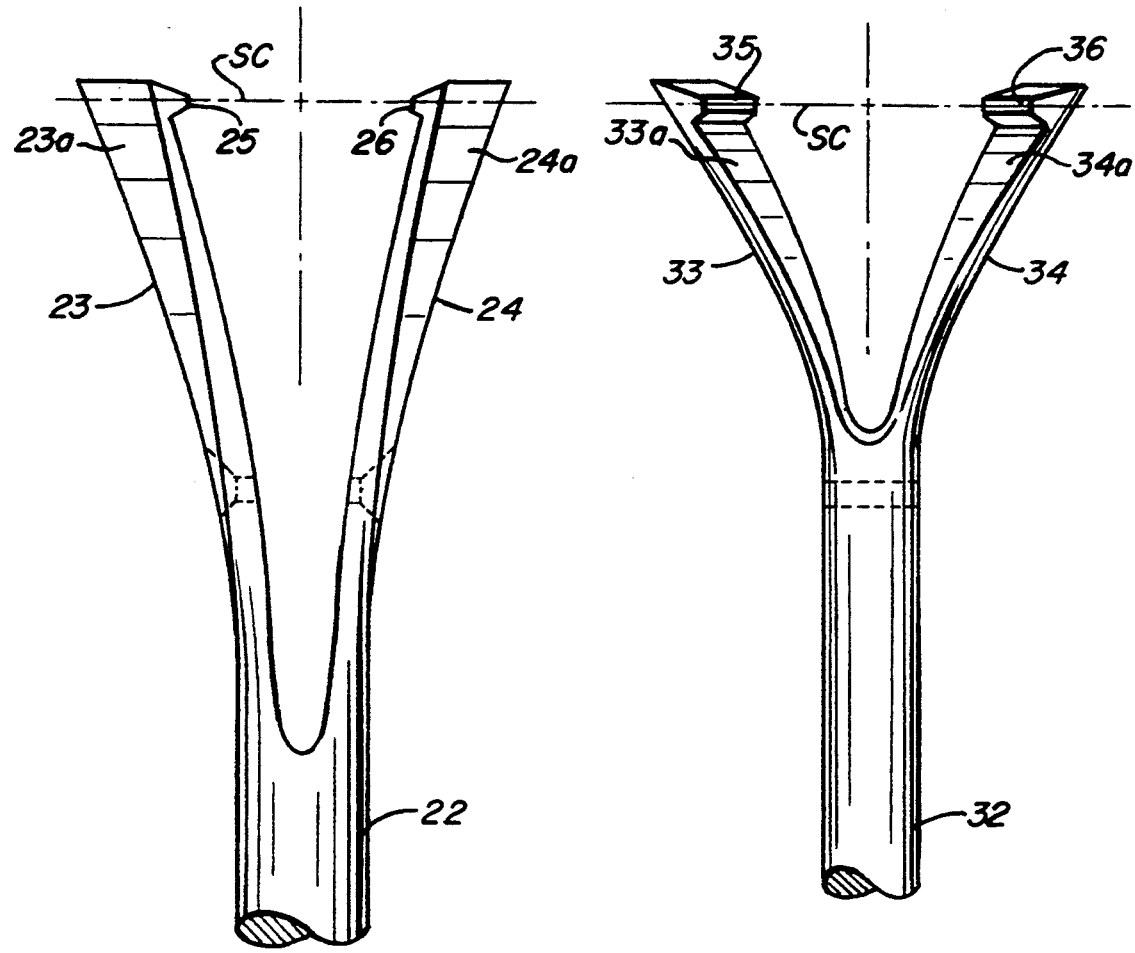
FIG.—4A  FIG.—4B

CERVICAL MANIPULATOR FORCEPS

BACKGROUND OF THE INVENTION

1. Field of the Invention

The present invention relates to medical devices, and more particularly, to manually operated forceps useful in the manipulation and examination of a female cervix.

2. Description of the Prior Art

The use of manipulative instruments in the course of examination of a patient, or in the course of a surgical procedure, are well known in the art. Thus, various forceps and retention devices have been developed in the past which, in one way or another, conform to the physiology of a person. Specific amongst these prior art devices are various forceps or tenacula of more or less general application and also various retention tools and forceps conformed for particular aspects of the patient's anatomy. Amongst these are various forceps or tenacula conformed for intra-vaginal use, including tenacula providing retention and forcing of the cervix in the course of abdominal hysterectomy.

One example of hysterectomy forceps is set out in the teachings of Shellhouse U.S. Pat. No. 2,583,892 in which semicircular, arcuate jaws are useful in grasping the cervix and also to delineate the cervico-vaginal juncture by upward pressure. While suitable for the purposes intended the foregoing forceps do not fully accommodate the range of exocervical dimensions, particularly where the exocervix is unusually small. Rev. Moreover, since the foregoing forceps are directed for abdominal hysterectomy procedures little or no visual and manipulative convenience is provided for vaginal hysterectomy.

Instruments useful during vaginal hysterectomy are exemplified in the teachings set out in U.S. Pat. No. 3,709,215 issued to Richmond in which suprapubic retractors are disclosed to provide visual and manipulative access to the cervix. While extremely useful in retraction and exposure of the vaginal vault, these teachings do not address the subsequent manipulative task of transvaginal excision.

The other prior art teachings, as exemplified in U.S. Pat. Nos. 4,120,302 to Ziegler; 3,779,248 to Karman; and 4,192,313 to Ogami all concern protective aspects in the course of cervical contact and thus do not address the forced manipulations entailed in the course of excision.

Thus, a forceps structure useful in the manipulation of the cervix during transvaginal removal of the uterus is generally required, and it is one such structure that is disclosed herein.

SUMMARY OF THE INVENTION

Accordingly, it is the general purpose and object of the present invention to provide a forceps structure conformed for cervical uterine manipulation which entails minimal visual obstruction.

Other objects of the invention are to provide a forceps structure useful in transvaginal hysterectomy procedures.

Yet further objects of the invention are to provide a forceps structure which is convenient in use, simple in fabrication, and separable into components for sterilization.

Briefly, these and other objects are accomplished within the present invention by providing a scissored arrangement of two forceps pieces each characterized by a handle and a tined grasping end. Preferably, each forceps piece is formed of stainless steel or similar metal construction selected both for sterilization convenience and a high elastic modulus. In this structural arrangement substantial grasping forces may be developed at the grasping ends while allowing for tine flexure in the course of forceps closure. This coordinated tine flexure, together with ball socket pivot ends, provides for a reduction in the spacing of the tines of each piece as the forceps is pivoted towards closure, thus accommodating a variety of cervical shapes.

More precisely, the upper tine pair extends for a substantial distance from a common shaft in the manner of two generally parallel, planar beams each offset in planform at the pivot axis defined by opposed hemispherical seats. The lower tine pair similarly emerges as forked set of beams split from a common shaft, of a longitudinal dimension lesser than the split of the upper tines. Both the upper and the lower tines are then twisted and bent towards their free ends to define grasping edges of a circular arc. A pivot shaft between two ball ends extends through the spherical seats in the upper tine pair and a pivot bore in the beams of the lower pair proximate their root juncture.

In consequence the pivotal motion of the two pieces towards each other advances the shaft of the lower tines into the gap between the upper tines. Since the point of this inward advancement is across the pivot from the tine ends, a concurrent inward deflection is obtained at the upper tines. The lower tines may be similarly flexed with pivotal motion by surface contact proximate the pivot. Of course, both shafts may be provided with loops and surfaces for manual convenience, and interlocks of any conventional form may be included for selective mechanical engagement.

BRIEF DESCRIPTION OF THE DRAWINGS

FIG. 1 is a perspective illustration of the inventive tenaculum, in its open extension;

FIG. 2 is another perspective illustration, separated by parts, of the tenaculum shown in FIG. 1;

FIG. 3 is a top view detail, taken in section along line 3—3 of FIG. 1; and

FIGS. 4A and 4B are each a top view of the tine portions of the inventive tenaculum.

DESCRIPTION OF THE PREFERRED EMBODIMENT

As shown in FIGS. 1-4, the inventive forceps or tenaculum, generally designated by the numeral 10, comprises a first forcep piece 11 and a second forcep piece 12, each of a generally elongate form and each formed of a metal or other hard material structure characterized by a high elastic modulus and substantially inert chemical properties. The forcep piece 11 includes a handle portion 21 formed at the end of a cylindrical shaft 22 which, at the other end, splits into two generally planar beams 23 and 24. Each of the beams 23 and 24 is of a generally planar construction, formed into a sheet or thin member, and thus will flex towards and away from each other upon the application of bending force. Beams 23 and 24, moreover, are twisted or deformed towards the free ends thereof, the twisted ends 23a and 24a being further bent or curled to present engagement edges 25 and 26 at each end. The alignment of each edge 25 and 26, by the twisting and bending, results in an edge orientation orthogonal to a 45 degree radius from the center of the shaft 22. Thus, the edges 25 and 26 align at the semicircle SC defined by the flexure of the tines.

In the lateral plane each beam 23 and 24 follows a stepped or off-set planform, with the offset located at the axes of two opposed ball seats 27 and 28, respectively in the exterior surfaces of beams 23 and 24, the beams then converging towards each other to form a tapered gap between the ball seat axes and the shaft 22.

The second forceps piece 12 is similarly constructed, including a shaft 32 from which two beams 33 and 34 branch out.

Once again, the beams 33 and 34 are twisted and bent in ends 33a and 34a which terminate in edges 35 and 36 defining the rest of the circle SC. The tapered spread between beams 33 and 34 is then engaged to the edges of beams 23 and 24 once the pieces 11 and 12 are pivotally engaged to each other. This pivotal engagement is effected by a shaft 41 extending through the ball seats 27 and 28 and a pivot bore 38 formed in the shaft 32, proximate the juncture with the beams 33 and 34. The ends of shaft 41 are then secured in pivot balls 42 and 43 marred in the corresponding seats.

In this manner the pivotal motion of shafts 22 and 32 effects a spreading between beams 23 and 24 at the juncture with the shaft while the free ends of the tines 33 and 34 are brought towards each other. Thus, the circle SC reduces in diameter as the handles 21 and 31 are pivoted together. In consequence a variety of cervical shapes may be accommodated and clamped by way of a conventional engagement mechanism 50 extending between shafts 22 and 32.

More importantly, the minimal structure of the beams and the minimal pivot architecture presents little visual obstruction within the vaginal vault. Thus, transvaginal hysterectomy is rendered more effective by the inventive forceps herein described.

Obviously many modifications and changes may be made to the foregoing without departing from the spirit of the invention. It is therefore intended that the scope of the invention be determined solely on the claims appended hereto.

What is claimed is:

1. A tenaculum useful in the manipulation and excision of a cervix and uterus comprising:

a first forcep piece characterized by a first handle, a first generally cylindrical arm extending from said first handle, said first arm extending into a pair of first split tines at the free end thereof diverging from said arm to form a tapered separation therebetween, each said first tine being formed and twisted to align the free edges thereof along first parts of a circle;

a second forcep piece characterized by a second handle, a second generally cylindrical arm extending from said second handle and aligned for receipt between said first tines within the interior of said tapered separation proximate the juncture thereof with said first arm, and including a pair of second tines at the free end of said second arm, said pair of second tines being formed as a split structure bent and twisted to align the free edges thereof along a second part of said circle; and pivot means extending through said first and said second arm for pivotal engagement thereof, said pivot means including a first and second ball seat formed in said first tines, a first and second ball receivable in the corresponding ones of said ball seat and a pivot rod connecting said first and second ball whereby the pivotal motion of said second arm into the juncture between said first tines affects the flexure thereof to reduce the spacing between the free ends of said first tines.

* * * * *